(12) United States Patent
Delnavaz et al.

(10) Patent No.: US 9,281,764 B2
(45) Date of Patent: Mar. 8, 2016

(54) ENERGY HARVESTER DEVICE FOR IN-EAR DEVICES USING EAR CANAL DYNAMIC MOTION

(71) Applicants: Aidin Delnavaz, Montréal (CA); Jérémie Voix, Montréal (CA)

(72) Inventors: Aidin Delnavaz, Montréal (CA); Jérémie Voix, Montréal (CA)

(*) Notice: Subject to any disclaimer, the term of this patent is extended or adjusted under 35 U.S.C. 154(b) by 498 days.

(21) Appl. No.: 13/867,518

(22) Filed: Apr. 22, 2013

(65) Prior Publication Data

US 2014/0312740 A1   Oct. 23, 2014

Related U.S. Application Data

(60) Provisional application No. 61/636,163, filed on Apr. 20, 2012.

(51) Int. Cl.
*H01L 41/113* (2006.01)
*H02N 2/18* (2006.01)
*A61F 11/08* (2006.01)

(52) U.S. Cl.
CPC ............ *H02N 2/18* (2013.01); *H01L 41/1134* (2013.01); *A61F 11/08* (2013.01); *H04R 2217/00* (2013.01); *H04R 2460/03* (2013.01)

(58) Field of Classification Search
CPC ......... H02N 2/18; H02N 2/183; H02N 2/186; F23Q 3/002; H04L 41/1136
USPC .......................................................... 310/339
See application file for complete search history.

(56) References Cited

U.S. PATENT DOCUMENTS

2007/0274558 A1* 11/2007 Lyon .............................. 381/424
2009/0209303 A1* 8/2009 Kroll et al. .................. 455/575.2
2012/0136197 A1* 5/2012 Van Gerwen .................... 600/25

* cited by examiner

*Primary Examiner* — Thomas Dougherty
(74) *Attorney, Agent, or Firm* — Equinox IP; Franz Bonsang

(57) ABSTRACT

An energy harvester device located into an in-ear device and harvesting energy from dynamic motion of the wall of the outer ear canal receiving the in-ear device therein, with an external sheath of the in-ear device generally assuming the contour of the ear canal wall. The energy harvester device has an energy harvesting module mounting on an inner portion of the in-ear device adjacent the external sheath, and is at least partially elastically deformable under a displacement of the ear canal wall to generate energy corresponding to the displacement of the wall. An energy storage module mounts onto the in-ear device and connects to the energy harvesting module to receive energy there from and supplying the stored energy to an electronic device of the in-ear device. The in-ear device having the energy harvester device therein is also part of the present invention.

15 Claims, 4 Drawing Sheets

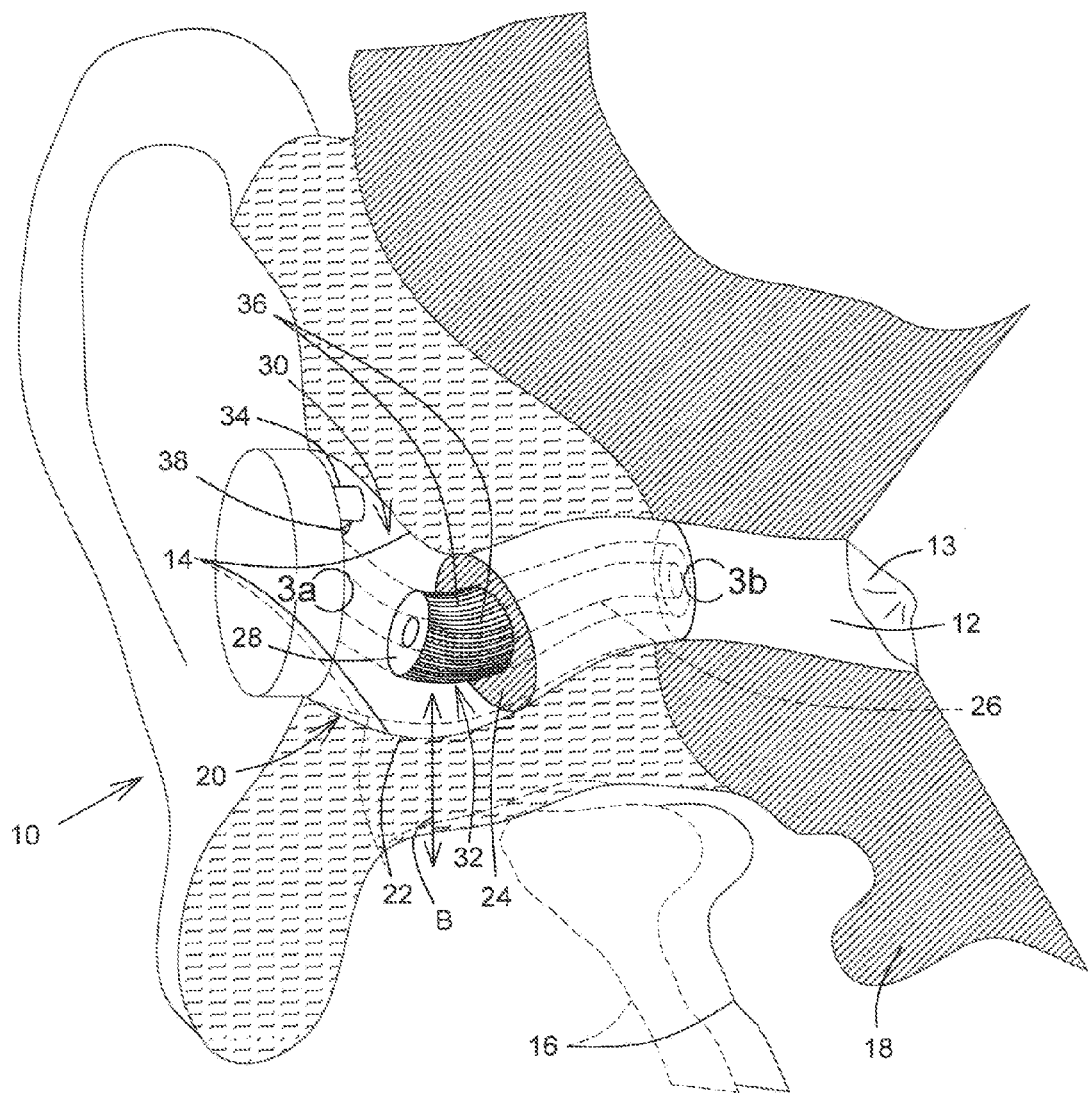
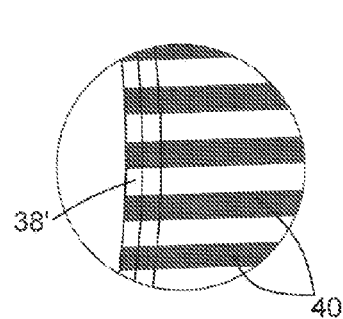 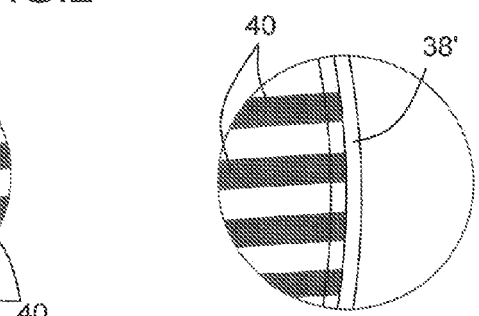
FIG.2
FIG.3a          FIG.3b

ENERGY HARVESTER DEVICE FOR IN-EAR DEVICES USING EAR CANAL DYNAMIC MOTION

CROSS REFERENCE TO RELATED APPLICATION

Benefit of U.S. Provisional Application for Patent Ser. No. 61/636,163 filed on Apr. 20, 2012, being incorporated herein by reference, is hereby claimed.

FIELD OF THE INVENTION

The present invention relates to energy harvesting, and more particularly to energy harvester devices and methods for generating energy from dynamic motion of the walls of an outer ear canal to supply power to an electronic/active in-ear device located therein, such as intra-aural active hearing protectors (earplugs), earphones, Bluetooth™ communication earpiece, or hearing-aid devices.

BACKGROUND OF THE INVENTION

The most limiting aspect in mobile technology is the electrical power supply. It restricts autonomy and has a direct impact on the weight and size of electronic devices. Most portable devices currently use batteries, although they are not of an environment friendly technology and they add considerable amount of volume and weight to portable devices. On the other hand extreme miniaturization of batteries is not convenient, since these batteries have to be changed frequently by users with limited finger dexterity, in the case of elderly people using hearing aids. Nonetheless, batteries will continue to be the main source of power in the near future, but energy harvesting technologies are gaining interest as alternatives to batteries. Energy harvesters, which obtain energy from external sources such as solar power, thermal energy or human power, provide small amounts of power and are usually suitable for low power portable devices. Wearable and implantable medical devices typically have low power consumption and strict size limitations. Hence, these are devices for which energy harvesting could be successfully applied. Among these types of devices are hearing aids and smart hearing protection devices, also called in-ear devices because they usually fit inside the ear canal. In addition, these have been substantially modified in recent years and are becoming less energy consuming. Furthermore, according to the World Health Organization, hundreds of millions of people are suffering from various types of hearing impairment and tens of millions of hearing aids are currently in use. Considerations such as these encourage further investigation as to using energy harvesting methods to power the electronic circuits of in-ear devices. Since the user wears the in-ear device, one possible power source would be the user and another would be the user's environment. In general, batteries and energy harvesting from the environment or the human body are the only possible ways to power in-ear devices.

Energy harvesting from human power has been extensively done using piezoelectric materials and rotary magnetic generators in relation with the swinging arm, walking (knee articulation and successive compressions of the sole below the ankle, etc.), but all these sources of energy are relatively far from any in-ear device and would nevertheless require wiring connection if used, thus creating discomfort to the user. Furthermore, these harvesting techniques typically generate more energy, namely milliwatts (mW) and more, than are required for a typical active in-ear device (as hearing-aid devices, smart hearing protection devices, and the like), in the order of a few microwatts ($\mu$W), but less than 1 mW.

Accordingly, there is a need for an improved energy harvester device for in-ear devices and an active in-ear device with such an energy harvester device therein.

SUMMARY OF THE INVENTION

It is therefore a general object of the present invention to provide an improved energy harvester device for in-ear devices, and the active in-ear device therewith.

An advantage of the present invention is that the energy harvester device can be integrated into the in-ear device for operation thereof.

Another advantage of the present invention is that the energy harvester device produces enough energy for the electrical needs of the active/electronic in-ear device to properly operate.

A further advantage of the present invention is that the energy harvester device is essentially transparent to the user (wearer) of the in-ear device (no electrical connection extending out from the in-ear device, no battery to periodically replace, no significant weight added to the in-ear device, and the like).

Still another advantage of the present invention is that the energy harvester device is well suited for use with a personalized active in-ear device that is inflatable to essentially assume the contour of the internal wall of the outer ear canal of the user, and therefore fit the shape of the user's ear canal.

Yet another advantage of the present invention is that the energy harvester device prevents the active in-ear device from having to be periodically placed onto a charging station, as it is often the case with rechargeable electronic in-ear devices like Bluetooth™ communication earpieces and the like.

Still another advantage of the present invention is that the energy harvester device allows the electronic in-ear device to be powered or recharged on purpose by a strong jaw-joint activity, such as chewing gum, eating a solid meal and the like.

According to an aspect of the present invention there is provided an energy harvester device for positioning into an in-ear device and harvesting energy from dynamic motion of a wall of an outer ear canal receiving the in-ear device therein, the in-ear device being adapted to be placed inside the outer ear canal of a user and having an external sheath substantially assuming a contour of the wall of the outer ear canal, said energy harvester device comprising:

an energy harvesting module for mounting on an inner portion of the in-ear device adjacent the external sheath, said energy harvesting module being at least partially elastically deformable under a displacement of the wall of the outer ear canal and generating energy corresponding to the displacement of the wall; and an energy storage module for mounting on the in-ear device and connecting to said energy harvesting module to receive energy therefrom, said energy storage module storing the received energy and being adapted to supply the stored energy to an electronic device of the in-ear device.

In one embodiment, the energy harvesting module includes a mechanical-to-electrical energy conversion film connecting to a pair of electrodes, said electrodes connecting to said energy storage module.

Conveniently, the mechanical-to-electrical energy conversion film includes at least one piezoelectric beam connecting to the pair of electrodes.

Conveniently, the energy harvesting module includes a plurality of piezoelectric beams each connecting to the pair of electrodes, said plurality of piezoelectric beams being positioned in a side-by-side relationship to one another and substantially forming at least a portion of a hollow cylindrical shape.

Conveniently, each electrode includes a ring located at a respective longitudinal end of said plurality of piezoelectric beams, each said ring having fingers extending along said plurality of piezoelectric beams.

Conveniently, the at least a portion of a hollow cylindrical shape is adapted for being embedded inside a settable area of the in-ear device between a rigid core thereof and the sheath, the settable area being adapted to receive a pressurized settable material therein that remains generally flexible once set so as to transmit at least a portion of the dynamic motion of the wall of the outer ear canal to the energy harvesting module.

Conveniently, the at least a portion of a hollow cylindrical shape is adapted for mounting onto a corresponding recess formed into the rigid core of the in-ear device.

In one embodiment, the energy harvesting module includes a mechanical-to-electrical energy system connecting to a pair of electrodes, said electrodes connecting to said energy storage module.

Conveniently, the mechanical-to-electrical energy system includes an electrical generator mounting onto a micro-turbine attachable to the in-ear device and drivable by an incompressible fluid located at least partially adjacent the sheath, said electrical generator electrically connecting to the pair of electrodes.

Conveniently, the mechanical-to-electrical energy system further includes a first fluid reservoir and a second fluid reservoir both in fluid communication with said micro-turbine via respective tubings, said first and second fluid reservoirs and said micro-turbine forming a closed-loop volume for the incompressible fluid, the mechanical-to-electrical energy system allowing the incompressible fluid to flow bidirectionally between said first and second fluid reservoirs.

Conveniently, the first and second fluid reservoirs are separated from one another by a bladder membrane.

Conveniently, the first and second fluid reservoirs are located in an upper region and a lower region of the in-ear device, respectively, both upper and lower regions being adjacent the sheath.

In one embodiment, the mechanical-to-electrical energy system includes:
  a first reservoir and a second reservoir both having a respective variable volume, said first and second reservoirs for mounting on the in-ear device adjacent to and away from the sheath, respectively;
  a tubing interconnecting both said first and second reservoirs to one another, said first and second reservoirs and said tubing forming a closed volume being filled with an incompressible fluid;
  a free cylindrical inner permanent magnet mounting inside said tubing and being freely displaceable therealong by the incompressible fluid flowing therein;
  first and second fixed annular outer permanent magnets mounting around said tubing between said inner permanent magnet and said first and second reservoirs, respectively, said first and second fixed annular outer permanent magnets magnetically maintaining said inner permanent magnet therebetween; and
  an electrical coil mounting around said tubing and said inner permanent magnet, said electrical coil connecting to said pair of electrodes.

Conveniently, the second reservoir is formed of an elastic membrane

According to another aspect of the present invention there is provided an active in-ear device being adapted to be placed inside an outer ear canal of a user, said in-ear device comprising:
  an external sheath mounting of a rigid core for substantially assuming a contour of a wall of the outer ear canal;
  an energy harvester device for harvesting energy from dynamic motion of the wall of the outer ear canal and being located into said in-ear device, said energy harvester device including:
    an energy harvesting module mounting on the rigid core of the in-ear device adjacent the external sheath, said energy harvesting module being at least partially elastically deformable under a displacement of the wall of the outer ear canal and generating energy corresponding to the displacement of the wall; and
    an energy storage module mounting on the in-ear device and connecting to said energy harvesting module to receive energy therefrom, said energy storage module storing the received energy and supplying the stored energy to an electronic device of the in-ear device.

Other objects and advantages of the present invention will become apparent from a careful reading of the detailed description provided herein, with appropriate reference to the accompanying drawings.

BRIEF DESCRIPTION OF THE DRAWINGS

Further aspects and advantages of the present invention will become better understood with reference to the description in association with the following Figures, in which similar references used in different Figures denote similar components, wherein:

FIG. 2 is a schematic section view of an energy harvester device for an in-ear device in accordance with a first embodiment of the present invention, showing the energy harvesting module with a mechanical-to-electrical energy conversion film embedded into the in-ear device adjacent to the external sheath thereof;

FIGS. 3a and 3b are partially broken enlarged schematic views taken along line 3a and line 3b of FIG. 2, respectively, showing the rings and fingers of the electrodes;

DETAILED DESCRIPTION OF THE INVENTION

With reference to the annexed drawings the preferred embodiment of the present invention will be herein described for indicative purposes and by no means as of limitation.

Figure 1:
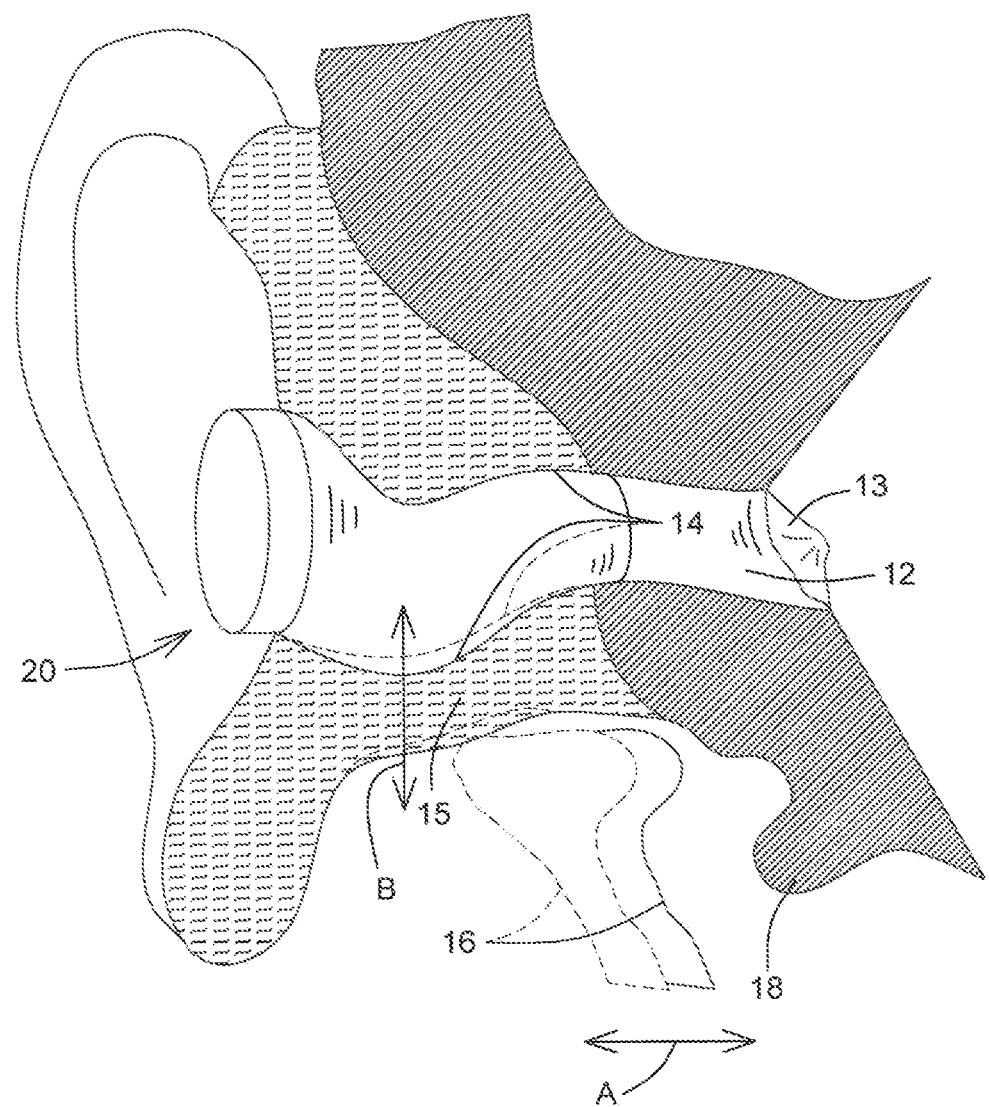
FIG. 1 is a schematic section view of an in-ear device located into the outer ear canal of the ear of a user, showing the dynamic motion (contraction and/or expansion, depending on the location in the canal relative to the tympanic membrane) of the internal wall of the outer ear canal upon displacement of the lower jaw bone (mandible) relative to the upper jaw bone (maxilla)

In reference to FIG. 1, there is schematically shown a typical deformation of the internal wall 14 of an outer ear canal 12 of a user of an in-ear device 20 under dynamic motion (represented by arrow B) of the internal wall 14, being in a cartilaginous region 15 adjacent the temporomandibular joint, caused by the movement (represented by arrow A) of the lower jaw bone (the mandible) 16 (represented by the ramus part thereof) relative to the fixed upper jaw bone (maxilla) adjacent to the fixed temporal bone 18 during eating, speaking and the like activities of the user, as shown by the solid and dashed lines. It is noted that during the displacement of the lower jaw bone 16 there is always a deformation B of cartilaginous region 15 and consequently of the internal wall 14, but the profile of the deformation B as shown in FIG. 1 is different to each person, and the expansion and/or contraction of the outer ear canal 12 further varies differently along the canal, from the tympanic membrane 13.

Referring to FIGS. 2 to 3b, there is shown an energy harvester device 30 in accordance with a first embodiment of the present invention. The energy harvester device 30 is typically positioned into an active in-ear device 20 (also an aspect of the present invention), at least partially, and harvests energy from dynamic motion B of the wall 14 of the outer ear canal 12 that receives the in-ear device 20 therein. The in-ear device 20 typically has an external sheath 22 that substantially assumes the contour of the wall 14 such that the in-ear device 20 is customized to the user.

The energy harvester device 30 includes an energy harvesting module 32 that mounts onto an inner portion (portion positionable inside the outer ear canal 14) of the in-ear device 20 adjacent the external sheath 22. The energy harvesting module 32 is adapted to be at least partially elastically deformable under a displacement B of the wall 14 of the outer ear canal 12, to generate energy corresponding and generally proportional to the displacement B of the wall 14. The energy harvester device 30 further includes an energy storage module 34 that typically mounts onto the in-ear device 20 and electrically connects to the energy harvesting module 32 to receive energy therefrom. The energy storage module 34 stores the electrical energy from the energy harvesting module 32 and is adapted to supply the stored energy to an electronic device (not shown) of the in-ear device 20 that requires power to operate.

The energy harvesting module 32 typically includes a mechanical-to-electrical energy conversion film, such as at least one, and preferably a plurality of relatively thin piezoelectric beams 36 (and typically slightly flexible) each electrically connecting to a pair of electrodes 38 that in turn electrically connect to the energy storage module 34. Typically, as better seen in FIGS. 3a and 3b, both electrodes 38 are located on longitudinal opposite ends of the piezoelectric beams 36 in the form of inner and outer rings 38' respectively and have fingers (illustrated as solid black stripes extending all along the in-ear device 20, partially broken and using broken lines in FIG. 2) 40 extending on top and bottom of the piezoelectric beams 36 respectively (with the top fingers extending from the outer ring and the inner fingers extending from the inner ring). Typically, the plurality of piezoelectric beams 36 are positioned in a side-by-side relationship to one another and substantially form at least an angular portion of, preferably an entire 360 degrees of a hollow cylindrical or windsock shape, as shown in FIG. 2.

In order to ensure that the energy harvesting module 32 is typically cast into the in-ear device 20 while no deformation is occurring thereon, it is preferable to embed the energy harvesting module 32 inside a settable area 24 (schematically represented by the cylindrical annular outer region) of the in-ear device 20 between a generally centrally located rigid core 26 thereof and the sheath 22. Furthermore, the settable area 24 is generally adapted to receive a pressurized settable material therein, that remains generally flexible once set (such as silicone-based material or the like), with the settable material being injected into the settable area 24 while the in-ear device 20 is preferably in-situ, i.e. properly installed into the outer ear canal 12 of the user. The flexibility of the settable material ensures that preferably at least a portion of the dynamic motion of the wall 14 of the outer ear canal 12 is transmitted to the energy harvesting module 32.

As more specifically shown in FIG. 2, the hollow cylindrical shape of the energy harvesting module 32 is adapted to mount onto a corresponding recess 28 formed into the rigid core 26 of the in-ear device 20.

Figure 4:
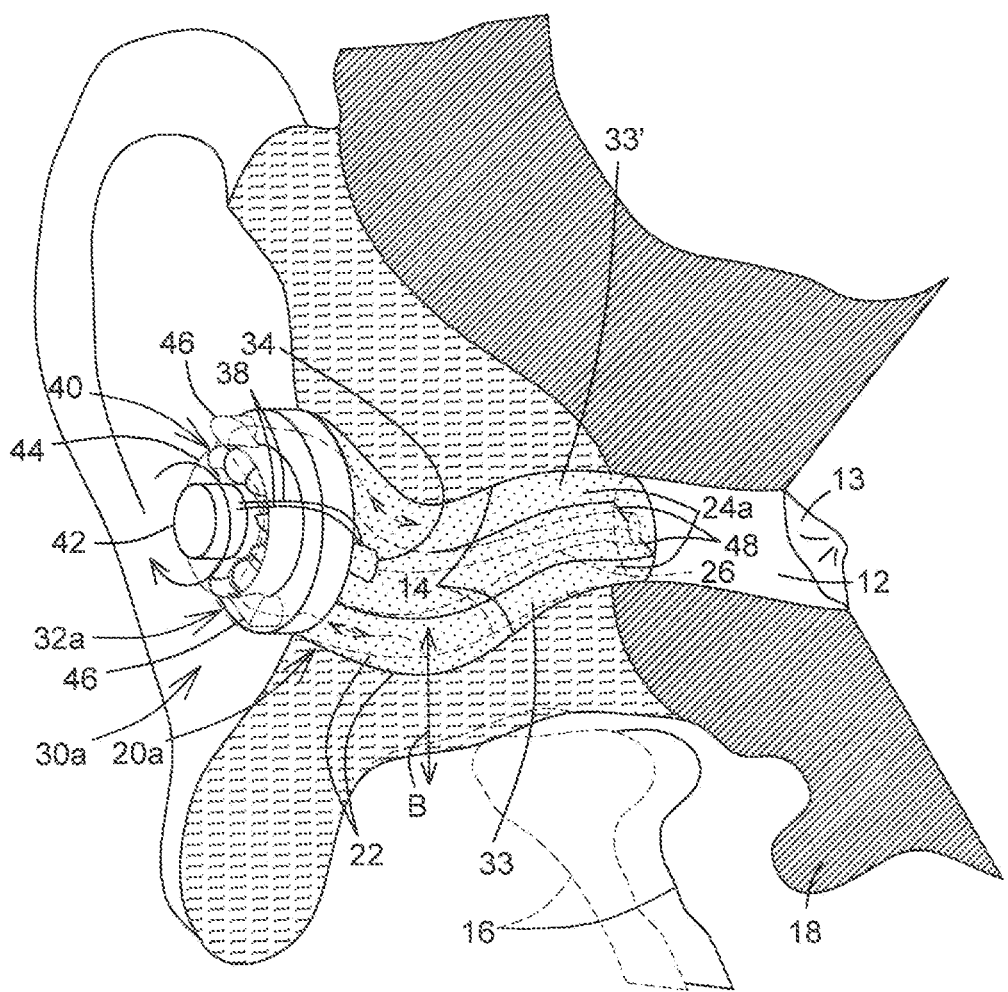
FIG. 4 is a schematic section view similar to FIG. 2 of a second embodiment of an energy harvester device for an in-ear device in accordance with the present invention, showing the energy harvesting module with a hydraulic-based mechanical-to-electrical energy system.

Now referring more specifically to FIG. 4, there is shown a second embodiment 30a of an energy harvester device in accordance with the present invention. The energy harvester device 30a has an energy harvesting module 32a typically made of a mechanical-to-electrical energy system that connects to the pair of electrodes 38 connecting to the energy storage module 34.

The mechanical-to-electrical energy system typically includes an electrical generator 42 electrically connecting to the pair of electrodes 38, and mounting onto a rotating shaft (not shown) of a micro-turbine 44 attachable to the in-ear device 20a, preferably to an extension of the rigid core 26 located outside of the outer ear canal 12, and drivable by an incompressible fluid (represented by the dot-type shading) located into a region 24a of the in-ear device 20a located at least partially adjacent the sheath 22.

Typically, the region 24a of the in-ear device 20a defines first lower 33 and second upper 33' fluid reservoirs of the mechanical-to-electrical energy system 32m. with both reservoirs 33, 33' in fluid communication with the micro-turbine 44 via respective tubing 46, such that the lower 33 and upper 33' fluid reservoirs and the micro-turbine 44 form a closed-loop volume for the incompressible fluid to flow remain therein. The flow (as represented by broken lines with arrows) of the incompressible fluid into the closed-loop volume between the two reservoirs 33, 33', is allowed in either direction depending on the relative pressure of the two reservoirs 33, 33', with the micro-turbine 44 always rotating in the same direction. Typically, the lower 33 and upper 33' fluid reservoirs are separated from one another by a bladder membrane 48 there between.

Figure 5:
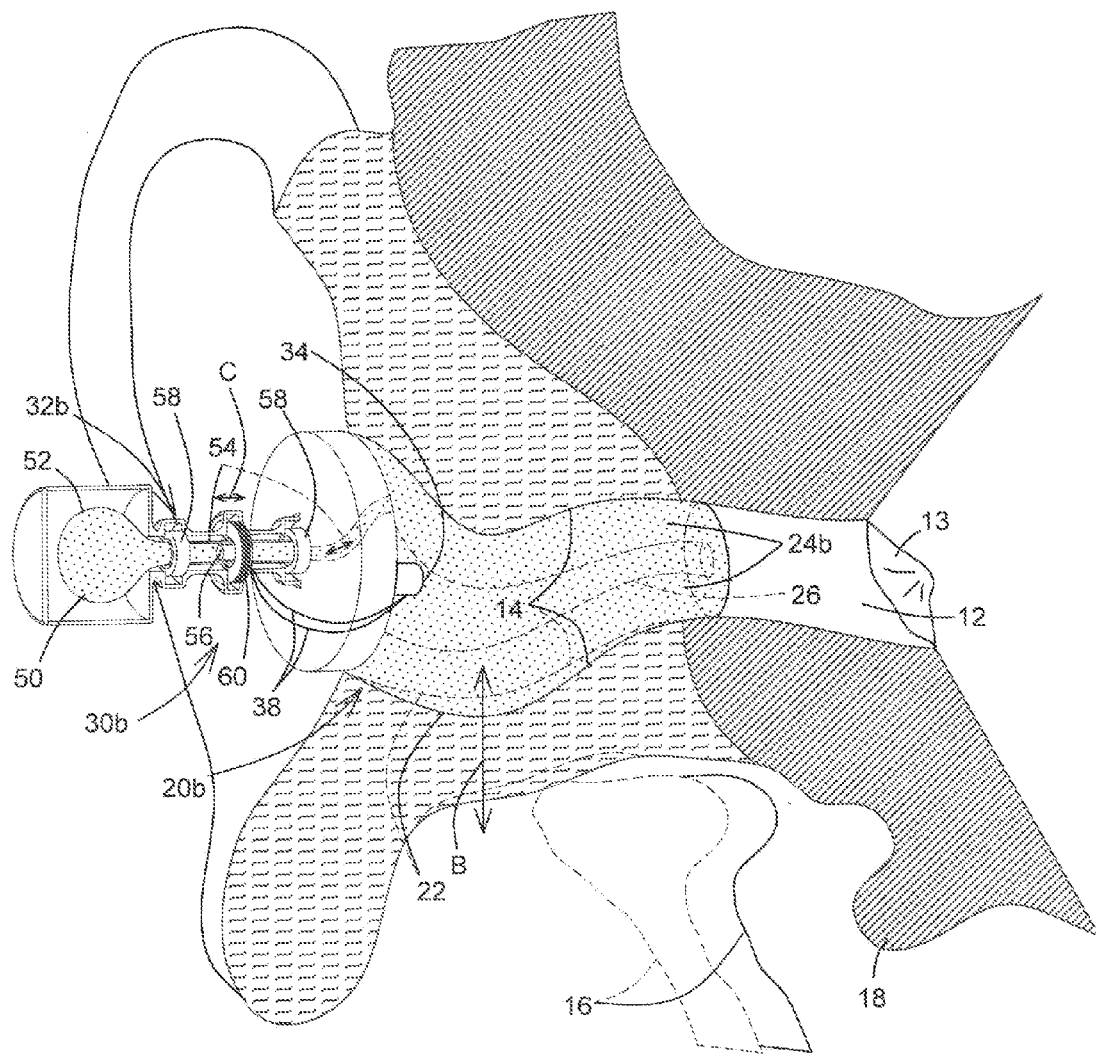
FIG. 5 is a schematic section view similar to FIG. 2 of a third embodiment of an energy harvester device for an in-ear device in accordance with the present invention, showing the energy harvesting module with a hydraulic/magnetic-based mechanical-to-electrical energy system.

Now referring more specifically to FIG. 5, there is shown a third embodiment 30b of an energy harvester device in accordance with the present invention. The energy harvester device 30b has its energy harvesting module 32b typically made of a mechanical-to-electrical energy system that includes a first reservoir 24b and a second reservoir 50 mounting respectively on the in-ear device 20b adjacent to and away from the sheath 22, and both having a respective variable volume. The variable volume of the first reservoir 24b is typically provided by the outer flexible sheath 22, and the variable volume of the second reservoir 50 is typically provided by an elastic outer membrane 52. A tubing 54 interconnects both first 24b and second 50 reservoirs to one another, and forms a closed volume therewith, which volume is filled with an incompressible fluid (again represented by the dot-type shading). A free cylindrical inner permanent magnet 56 mounts inside the tubing 54 and is freely displaceable therealong by the incompressible fluid flowing therein (as represented by arrow C). First and second fixed annular outer permanent magnets 58 mount around the tubing 54 between the inner permanent magnet 56 and a respective one of the first 24b and second 50 reservoirs. The first and second fixed annular outer permanent magnets 58 magnetically maintain the inner permanent magnet 56 therebetween; with their magnetic poles repulsing the corresponding magnetic pole of the inner permanent magnet 56. An electrical coil 60, electrically connecting to the pair of electrodes 38, mounts around the tubing 54 and the inner permanent magnet 56. The displacement of the inner magnet 56 by the incompressible fluid flowing back and forth inside the tubing 54 because of the dynamic motion of the wall 14 of the ear canal 12 compressing the sheath 22 and the stretched elastic membrane 52 of the second reservoir 50, and biased by the two outer magnets 58, induces electric current into the coil 60.

In FIG. 5, although the magnets 56, 58, the coil 60 and the second reservoir 50 are schematically shown outside of the in-ear device 20*b* and attached to the rigid core 26 thereof, they all could also be located and therefore hidden inside the rigid core 26 or an extension thereof (not shown) without departing from the scope of the present invention.

Although the present invention has been described with a certain degree of particularity, it is to be understood that the disclosure has been made by way of example only and that the present invention is not limited to the features of the embodiments described and illustrated herein, but includes all variations and modifications within the scope of the invention as hereinafter claimed.

We claim:

1. An energy harvester device for positioning into an in-ear device and harvesting energy from dynamic motion of a wall of an outer ear canal receiving the in-ear device therein, the in-ear device being adapted to be placed inside the outer ear canal of a user and having an external sheath substantially assuming a contour of the wall of the outer ear canal, said energy harvester device comprising:
    an energy harvesting module for mounting on an inner portion of the in-ear device adjacent the external sheath, said energy harvesting module being at least partially elastically deformable under a displacement of the wall of the outer ear canal and generating energy corresponding to the displacement of the wall; and
    an energy storage module for mounting on the in-ear device and connecting to said energy harvesting module to receive energy therefrom, said energy storage module storing the received energy and being adapted to supply the stored energy to an electronic device of the in-ear device.

2. The energy harvester device of claim 1, wherein the energy harvesting module includes a mechanical-to-electrical energy conversion film connecting to a pair of electrodes, said electrodes connecting to said energy storage module.

3. The energy harvester device of claim 2, wherein the mechanical-to-electrical energy conversion film includes at least one piezoelectric beam connecting to the pair of electrodes.

4. The energy harvester device of claim 3, wherein the energy harvesting module includes a plurality of piezoelectric beams each connecting to the pair of electrodes, said plurality of piezoelectric beams being positioned in a side-by-side relationship to one another and substantially forming at least a portion of a hollow cylindrical shape.

5. The energy harvester device of claim 4, wherein each said electrode includes a ring located at a respective longitudinal end of said plurality of piezoelectric beams, each said ring having fingers extending along said plurality of piezoelectric beams.

6. The energy harvester device of claim 4, wherein the at least a portion of a hollow cylindrical shape is adapted for being embedded inside a settable area of the in-ear device between a rigid core thereof and the sheath, the settable area being adapted to receive a pressurized settable material therein that remains generally flexible once set so as to transmit at least a portion of the dynamic motion of the wall of the outer ear canal to the energy harvesting module.

7. The energy harvester device of claim 6, wherein the at least a portion of a hollow cylindrical shape is adapted for mounting onto a corresponding recess formed into the rigid core of the in-ear device.

8. The energy harvester device of claim 1, wherein the energy harvesting module includes a mechanical-to-electrical energy system connecting to a pair of electrodes, said electrodes connecting to said energy storage module.

9. The energy harvester device of claim 8, wherein the mechanical-to-electrical energy system includes an electrical generator mounting onto a micro-turbine attachable to the in-ear device and drivable by an incompressible fluid located at least partially adjacent the sheath, said electrical generator electrically connecting to the pair of electrodes.

10. The energy harvester device of claim 9, wherein the mechanical-to-electrical energy system further includes a first fluid reservoir and a second fluid reservoir both in fluid communication with said micro-turbine via respective tubings, said first and second fluid reservoirs and said micro-turbine forming a closed-loop volume for the incompressible fluid, the mechanical-to-electrical energy system allowing the incompressible fluid to flow bidirectionally between said first and second fluid reservoirs.

11. The energy harvester device of claim 10, wherein the first and second fluid reservoirs are separated from one another by a bladder membrane.

12. The energy harvester device of claim 10, wherein the first and second fluid reservoirs are located into an upper region and a lower region of the in-ear device, respectively, both upper and lower regions being adjacent the sheath.

13. The energy harvester device of claim 8, wherein the mechanical-to-electrical energy system includes:
    a first reservoir and a second reservoir both having a respective variable volume, said first and second reservoirs for mounting on the in-ear device adjacent to and away from the sheath, respectively;
    a tubing interconnecting both said first and second reservoirs to one another, said first and second reservoirs and said tubing forming a closed volume being filled with an incompressible fluid;
    a free cylindrical inner permanent magnet mounting inside said tubing and being freely displaceable therealong by the incompressible fluid flowing therein;
    first and second fixed annular outer permanent magnets mounting around said tubing between said inner permanent magnet and said first and second reservoirs, respectively, said first and second fixed annular outer permanent magnets magnetically maintaining said inner permanent magnet therebetween; and
    an electrical coil mounting around said tubing and said inner permanent magnet, said electrical coil connecting to said pair of electrodes.

14. The energy harvester device of claim 13, wherein the second reservoir is formed of an elastic membrane.

15. An active in-ear device being adapted to be placed inside an outer ear canal of a user, said in-ear device comprising:
    an external sheath mounting of a rigid core for substantially assuming a contour of a wall of the outer ear canal;

an energy harvester device for harvesting energy from dynamic motion of the wall of the outer ear canal and being located into said in-ear device, said energy harvester device including:

an energy harvesting module mounting on the rigid core of the in-ear device adjacent the external sheath, said energy harvesting module being at least partially elastically deformable under a displacement of the wall of the outer ear canal and generating energy corresponding to the displacement of the wall; and an energy storage module mounting on the in-ear device and connecting to said energy harvesting module to receive energy therefrom, said energy storage module storing the received energy and supplying the stored energy to an electronic device of the in-ear device.

* * * * *